(12) United States Patent
Cochran

(10) Patent No.: US 9,011,449 B1
(45) Date of Patent: Apr. 21, 2015

(54) SCREW AND ROD FIXATION SYSTEM

(76) Inventor: Scott Cochran, Birmingham, AL (US)

(*) Notice: Subject to any disclaimer, the term of this patent is extended or adjusted under 35 U.S.C. 154(b) by 590 days.

(21) Appl. No.: 13/080,482

(22) Filed: Apr. 5, 2011

(51) Int. Cl.
  *A61B 17/88* (2006.01)
  *A61B 17/86* (2006.01)

(52) U.S. Cl.
  CPC ..................................... *A61B 17/86* (2013.01)

(58) Field of Classification Search
  USPC .................................................. 606/246–279
  See application file for complete search history.

(56) References Cited

U.S. PATENT DOCUMENTS

| | | | |
|---|---|---|---|
| 6,251,111 B1 * | 6/2001 | Barker et al. ................ | 606/86 A |
| 6,740,086 B2 * | 5/2004 | Richelsoph ....................... | 606/60 |
| 7,922,724 B2 * | 4/2011 | Lim ............................ | 606/86 A |
| 8,623,061 B2 * | 1/2014 | Quevedo et al. .............. | 606/272 |
| 2005/0090824 A1 * | 4/2005 | Shluzas et al. .................. | 606/61 |
| 2007/0078460 A1 * | 4/2007 | Frigg et al. ....................... | 606/61 |
| 2008/0051794 A1 * | 2/2008 | Dec et al. ......................... | 606/73 |
| 2008/0177269 A1 * | 7/2008 | Seelig .............................. | 606/90 |
| 2009/0157125 A1 * | 6/2009 | Hoffman et al. ............. | 606/86 A |
| 2011/0087298 A1 * | 4/2011 | Jones ............................ | 606/86 A |
| 2011/0125196 A1 * | 5/2011 | Quevedo et al. .............. | 606/308 |
| 2011/0218581 A1 * | 9/2011 | Justis ........................... | 606/86 A |

* cited by examiner

*Primary Examiner* — Jerry Cumberledge
(74) *Attorney, Agent, or Firm* — C. Brandon Browning; Maynard, Cooper & Gale, PC

(57) ABSTRACT

A pedicle screw and rod fixation assembly including a pair of opposing tabs having a proximal end and a distal end, the pair of opposing tabs being coupled to one another about the distal end thereof by a screw head member, a decoupling mechanism for decoupling the pair of opposing tabs from the screw head member, a rod receiving slot between the pair of opposing tabs, and a sliding member configured for coupling to the pair of opposing tabs. The sliding member and the pair of opposing tabs are configured for allowing movement of the sliding member distally along the pair of opposing tabs and preventing movement of the sliding member proximally along the pair of opposing tabs.

31 Claims, 9 Drawing Sheets

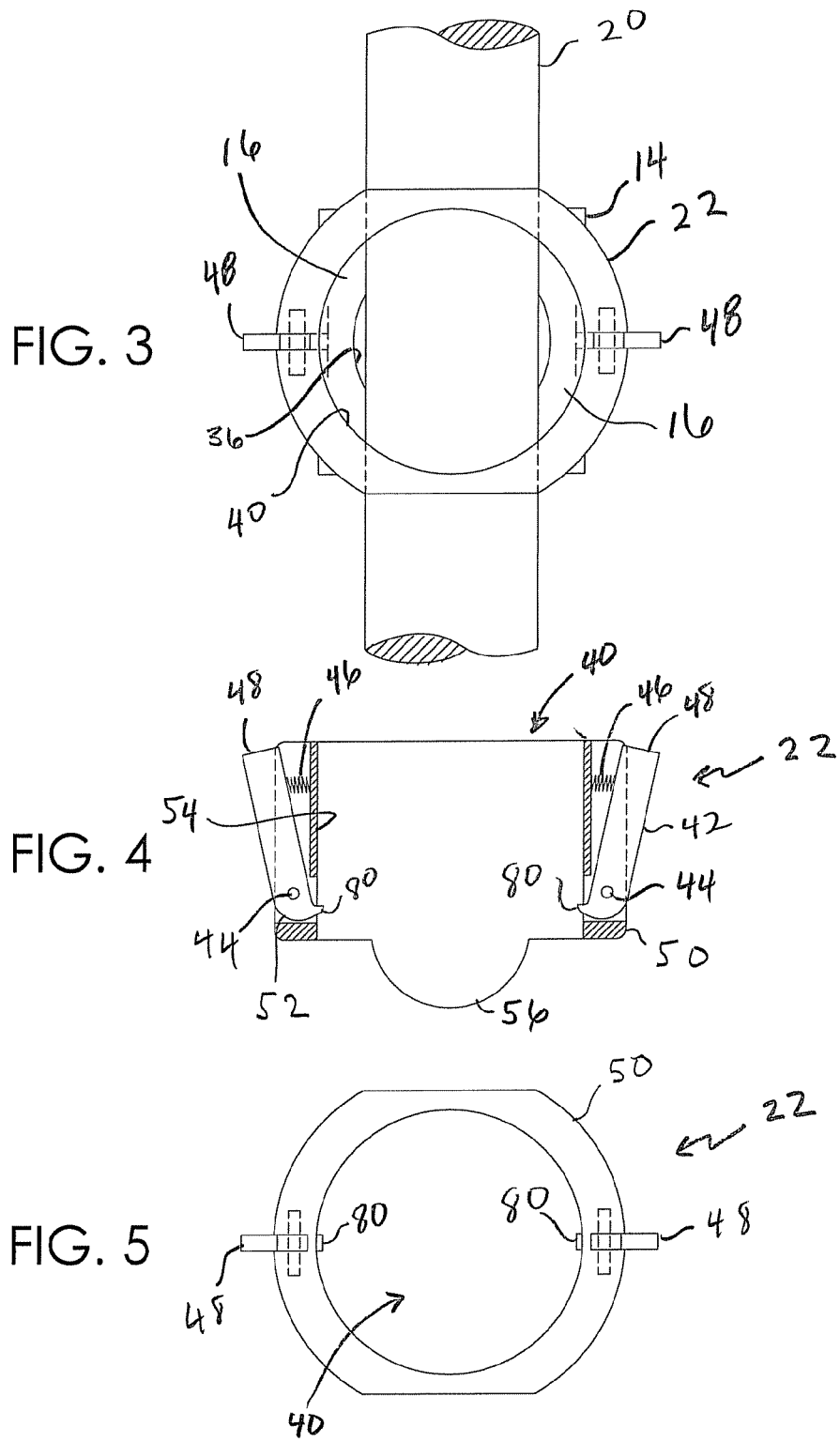

SCREW AND ROD FIXATION SYSTEM

FIELD OF THE INVENTION

The present invention relates to spinal implants. More particularly, the present invention relates to screw fixation assemblies for use with bone fixation systems.

BACKGROUND OF THE INVENTION

Spinal deformity surgery is a complex technical procedure that can involve numerous implants and techniques to achieve a straightening of the spine in three dimensions. There is a sagital plane that may contain an increased or decreased lordosis or kyphosis, a coronal plane that may contain a left/right curvature of the spine and an axial plane that may contain a rotational deformity. All three planes must be addressed if a result that leaves the patient functional and provides acceptable cosmesis is to be achieved.

Current techniques involve the use of pedicle screws and various hooks as anchors or fixation points along the posterior spine. Screw types can include polyaxial screws, fixed angle or monoaxial screws and uniplanar screws. Each screw type has a feature set that can be useful in various situations. As such, surgeons will select a screw type for a particular procedure based upon the problems to be addressed and the feature set of the screw type.

Following placement of the fixation points by a physician, the corrective part of the procedure occurs when a rod is introduced into each of the fixation points along the spine. Except in extreme cases, a single "correcting" rod is placed first on one lateral side of the spine, followed by second "stabilizing" rod on the other lateral side of the spine. The rod is contoured to a shape that closely approximates the natural contour of a non-deformed spine. After the rods are introduced into the fixation points, the physician forces the fixation point to meet the rod so that the rod can be locked into the fixation point, which may be a screw or a hook, to hold the spine in a more normal position.

In certain cases, the physician is unable to introduce the rod into all of the fixation points or bring the rod and fixation points together. This can occur if the spine is severely deformed which causes the fixation points to be misaligned. When this occurs, the physician bends the rod in such a way that it can be introduced into the fixation points, but this compromises the correction.

Bending of the rod "in situ" can be used to provide more correction after the rod is seated into all of the fixation points. Obviously, the introduction of a rod into a deformed spine can be very challenging to do so there have been many instruments designed to help forcibly bring the spine and the rod together. Often, when an instrument is used to force the mating of the rod and anchor, the anchor can pull out of the bone because the force is too great. Also, while reducing the rod into one anchor, it may miss the anchor above or below because the alignment of the rod and the spine do not match. In this case, the rod must be released from the anchor and re-introduced taking care, and often another set of hands, to guide the rod into the adjacent anchors during reduction.

Reduction screws have been used widely for some time to aide in the introduction of a rod into a fixation point and forcing of the rod into a seat of the screw. Reduction screws have extended arms or tabs that are threaded so that a set screw can be introduced into the extended tabs for securing the rod into the screw before the rod is fully seated in the screw seat. By turning the set screw, the rod is driven down the extension tabs and into the screw seat of the screw head in a controlled and progressive manner.

A shortcoming of current reduction screws is that a physician utilizing a reduction screw must turn the set screw ten to fifteen complete turns to seat the rod. Since it is not uncommon for twenty or more screws to be used during a corrective spine surgery, reduction screws are underused as physicians are reluctant to invest the time and effort required to turn the set screws three hundred times. Another shortcoming of reduction screws is that their extension tabs rarely extend longer than approximately one inch. This is in part due to the additional set screw advancement, i.e., complete set screw turns, required when longer extension tabs are used. Further, longer extension tabs are prone to "splay" when reduction forces are applied. This can cause the set screw to disengage or cross-thread. Instruments have been designed to control the splaying effect, but they tend to complicate the procedure. Yet another shortcoming of reduction screws is that the amount of torque they require to drive a rod into the screw seat is difficult to translate into actual downward force by the physician. A few inch pounds of torque created by rotating a screwdriver handle can equate to over one hundred pounds of force on the screw. This can cause the pedicle screw to pull out of the bone thus causing the loss of a fixation point.

SUMMARY OF THE INVENTION

The screw and rod fixation system of the present invention improves the procedure for correcting defective spines by providing enhanced reduction capabilities without adding the need to drive a set screw the entire length of every extended tab. The reduction mechanism can be made much longer which facilitates rod introduction along the entire length of the spine prior to any forces being applied. Splaying of the extended tabs is not an issue because a collar prevents the tabs from splaying outward and the rod prevents inward splay. This also allows for the simultaneous introduction of two separate rods which reduces the amount of localized force on any given anchor and distributes the corrective load among many of the anchors.

More particularly, each pedicle screw is anchored in a vertebra in the standard fashion. The extended tabs can be integrated into the screw when it is manufactured, or the extended tabs can be provided as a temporary extension that is placed onto the screw during surgery and removed when a rod is fully seated. The integral extended tabs are broken off at the end of the surgery as is typical of existing reduction screws. Where two adjacent rods are being implanted, both rods are introduced into the slots formed by the extended tabs for each screw as a first step. Collars are then placed onto the extended tabs to capture the rods into the extended tabs. At this point, both rods are in place with little or no force being applied to the spine.

Reduction of the rods into the bottom of the screw heads is carried out by pushing the collars down toward the base of the screw heads by hand or with an instrument designed for this purpose. As the rods begin to encounter resistance, the spine begins to move in small increments toward the rods. As the collars are pushed farther down, a ratcheting action between the collars and the extended tabs retains the rods in place and prevents them from sliding back up the extended tabs. This allows the physician to sequentially move up and down the spine from screw to screw and on both sides of the spine to push the collars down on the extended tabs with an appropriate amount of force based on the number of anchors, bone quality, anchor quality etc.

Since this initial reduction is by hand the force applied is 1:1 such that the exact downward force applied by the surgeon is the same force retained by the collar when the surgeon releases pressure. This offers improved tactile feedback in a reduction maneuver over the prior art. The present invention also allows for distribution of the corrective forces over the entire spine thereby reducing the chances of screw pullout.

As manual reduction continues, instruments that apply more force than can be generated manually can be used to progressively force the collars farther down the extended tabs in a controlled fashion. To continue to distribute the forces, multiple instruments can be used simultaneously such that a single anchor does not receive excessive force. Alternatively, as increased reduction force is applied with an instrument, an assistant can manually advance the collars on the anchors adjacent to the persuader instrument to immediately disperse the force to multiple anchors. Alternatively, a physician can choose to initially place a single rod with this technique and subsequently place the second rod. The benefits are the same except that the corrective forces are not shared by the second rod, therefore increasing the load on the anchors of the first rod placed.

When the rod reaches its final position in the screw heads, set screws are introduced to hold the achieved correction. The tabs and collars are then removed. Rod rotation and in situ bending can now be employed to achieve adjustments to the final correction, as with standard implants.

According to one aspect of the present invention, there is provided a screw and rod fixation assembly including a pair of opposing tabs having a proximal end and a distal end, the pair of opposing tabs being coupled to one another about the distal end thereof by a screw head member. The assembly further includes a decoupling mechanism for decoupling the pair of opposing tabs from the screw head member, a rod receiving slot between the pair of opposing tabs, and a sliding member configured for coupling to the pair of opposing tabs. The sliding member and the pair of opposing tabs are configured for allowing movement of the sliding member distally along the pair of opposing tabs and preventing movement of the sliding member proximally along the pair of opposing tabs.

According to another aspect of the invention, there is provided an assembly including extension tabs detachably coupled to a pedicle screw head, a rod receiving slot formed between the extension tabs, a collar, and a ratchet mechanism configured for preventing movement in a predetermined direction between the collar and the extension tabs. The ratchet mechanism is coupled to and between the collar and the extension tabs and includes at least one pawl that is biased toward a central axis of the collar. In use, a rod is inserted into the rod receiving slot, the extension tabs are inserted through an opening in the collar, the collar is slid along the extension tabs toward the screw head, and the ratchet mechanism is used to prevent movement of the collar away from the screw head.

According to yet another aspect of the invention, there is provided a method for reduction of a rod into a screw having detachable extension tabs. The method includes inserting the rod within a slot formed between the extension tabs, coupling a sliding member to the extension tabs, pressing the sliding member against the rod and sliding the sliding member and rod together toward the screw. When the rod exerts a force against the sliding member, the sliding member is prevented from sliding along the extension tabs away from the screw by a ratchet mechanism.

BRIEF DESCRIPTION OF THE DRAWINGS

FIG. 3 is a top plan view of the screw and rod fixation assembly of FIG. 1

FIG. 4 is a sectional view of a ratchet collar of the screw and rod fixation assembly of FIG. 1

FIG. 5 is a top plan view of the collar of FIG. 5.

DETAILED DESCRIPTION OF PRESENTLY PREFERRED EMBODIMENTS

Figure 1:
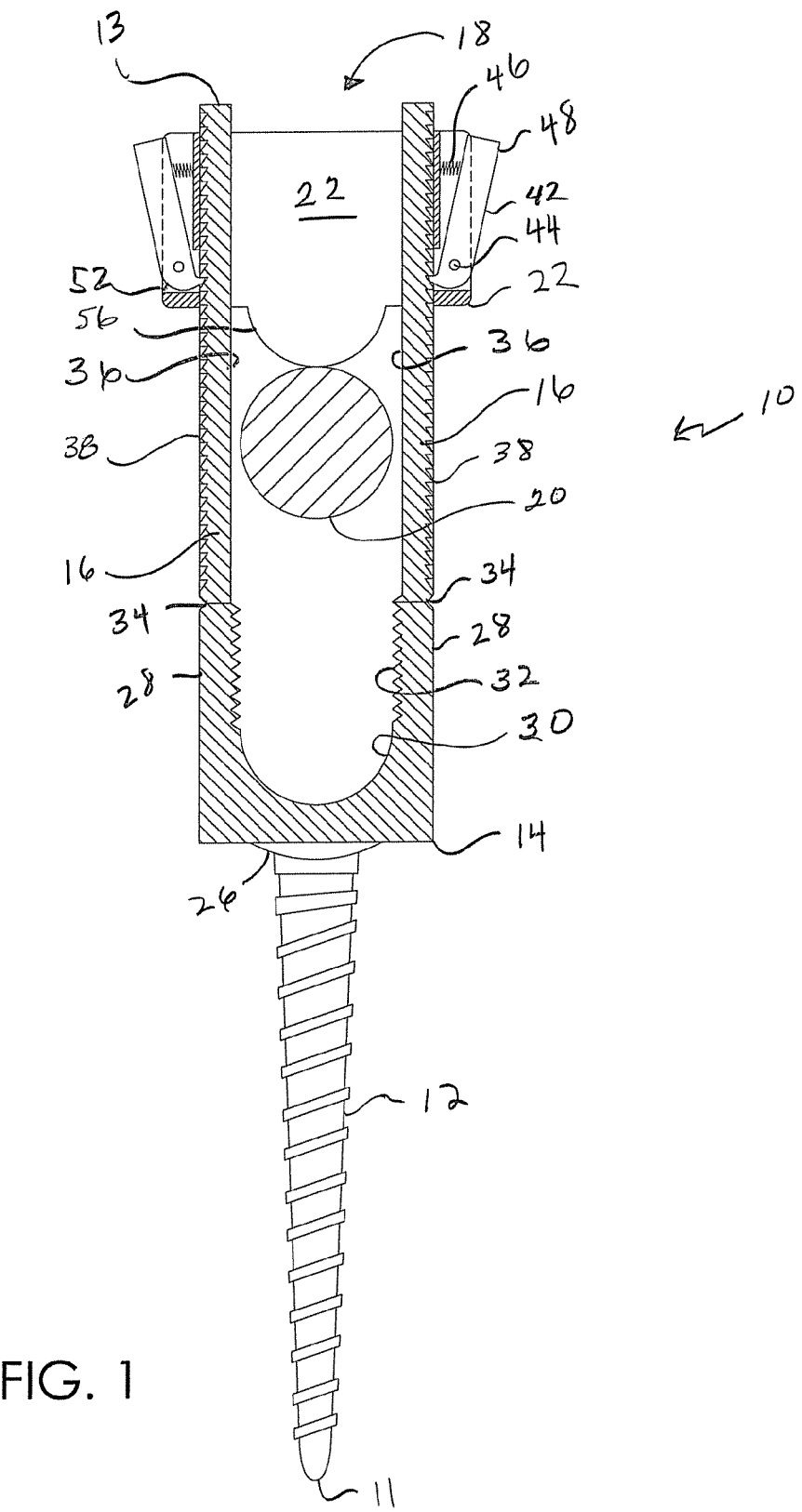
FIG. 1 is a sectional view of a screw and rod fixation assembly in accordance with a preferred embodiment of the present invention.

FIGS. 1 through 13 illustrate a screw and rod fixation assembly 10 and various parts thereof in accordance with a preferred embodiment of the present invention. Generally, assembly 10 includes a distal end 11, a pedicle screw 12 having a screw head 14, a proximal end 13, a pair of opposing extension tabs 16 detachably coupled to screw head 14, a rod receiving slot 18 defined between extension tabs 16, a rod 20 slideably received within slot 18, a ratchet collar 22 pressed against rod 20 and coupled to tabs 16 in a manner allowing movement of collar 22 distally along tabs 16 while preventing movement thereof proximally and a set screw 24 for locking rod 20 within screw head 14.

Figure 2:
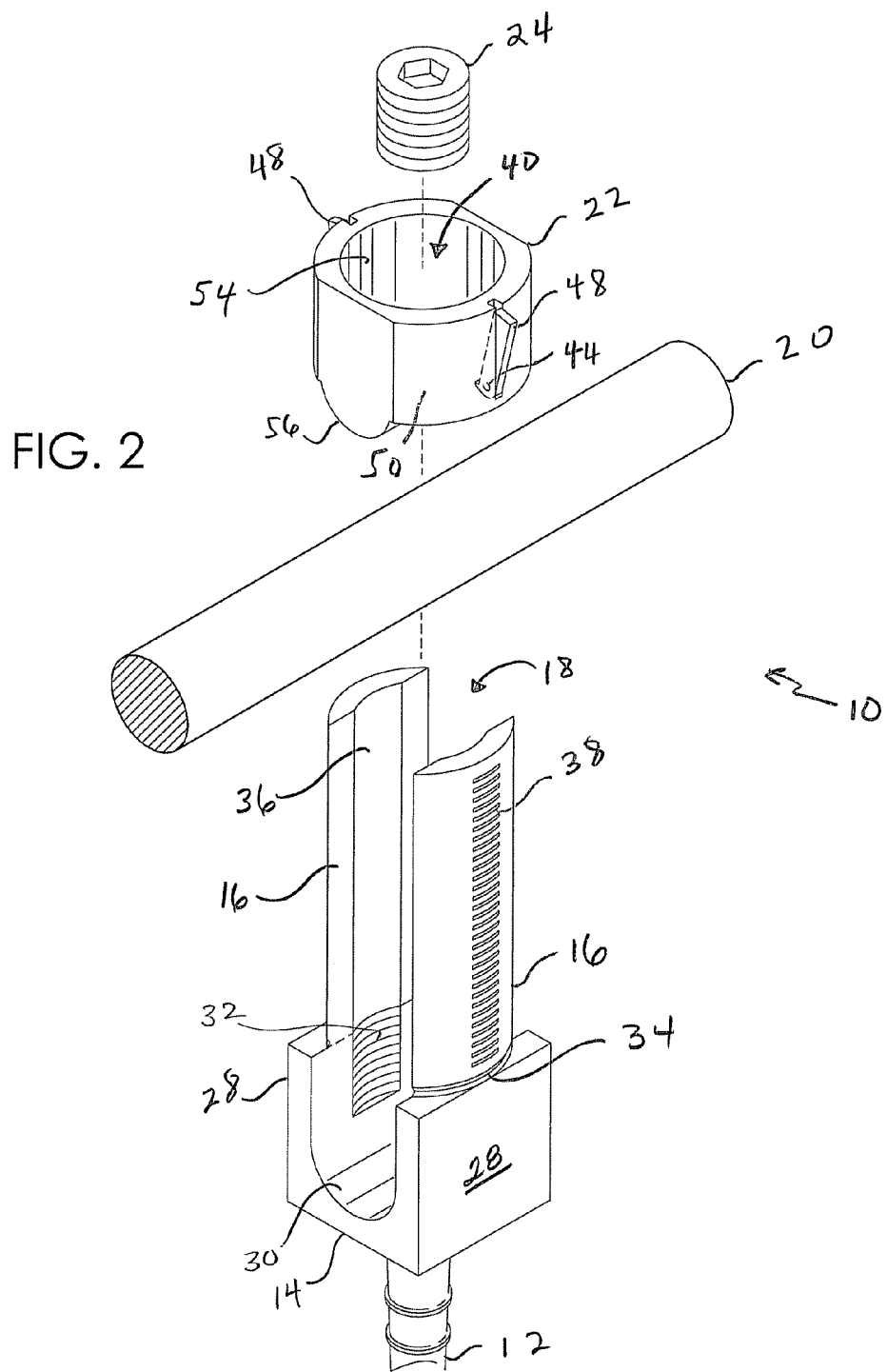
FIG. 2 is an exploded perspective view of the screw and rod fixation assembly of FIG. 1 displaying a set screw.
Figure 6:
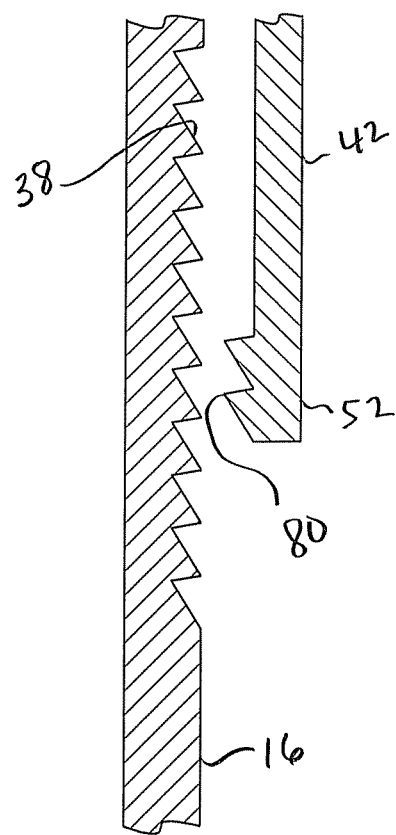
FIG. 6 is sectional view of a ratchet collar pawl of the ratchet collar of the screw and rod fixation assembly of FIG. 1 and corresponding ratchet grooves.

More particularly, referring to FIGS. 1 and 2, screw 12 can be any size, shape or design as is known to those of skill in the art for anchoring to bone. Screw 12. In the preferred embodiment, screw 12 is a monoaxial pedicle screw and is therefore integrally formed with screw head 14 which is axially aligned with a longitudinal axis of screw 12. In this embodiment, relative movement between screw 12 and screw head 14 is not allowed. In an alternative embodiment, screw 12 may be a polyaxial screw where screw head 14 is pivotably mounted to an upper end 26 of screw 12. In this embodiment, screw head 14 is allowed to pivot about screw 12 which can reduce stress on the spinal column during rod reduction.

Extending proximally from opposing sides of screw head 14 are a pair of opposing tabs 28. Tabs 28 form there between, along the inner surfaces thereof, a U-shaped rod seat 30 having proximally extending, opposing, arcuate-shaped walls for receiving rod 20 from rod receiving slot 18 and guiding rod 20 into screw head 14. The distance between the proximally extending walls is substantially the same as the diameter of rod 20 so that rod 20 can be snuggly received within rod seat 30. To maintain or lock rod 20 within rod seat 30, the proximally extending walls of rod seat 30 include threaded portions 32 that are arranged there along for receiving set screw 24. Threaded portions 32 do not extend proximally along extension tabs 16 and are configured so that locking rod 20 within rod seat 30 requires fewer turns of set screw 24 than current pedicle screws.

Detachably coupled to the proximal ends of tabs 28 are extension tabs 16. Tabs 28 are separated from extension tabs 16 by notches 34 which enable tabs 16 to be readily removed from tabs 28. Like tabs 28, extension tabs 16 have proximally extending, opposing, arcuate-shaped walls for receiving rod 20 and guiding rod 20 into screw head 14. However, unlike tabs 28, the proximally extending walls of extension tabs 16 have smooth inner surfaces 36, which together define there between slot 18. Further, the proximally extending walls of extension tabs 16 are separated by a greater distance than the proximally extending walls of tabs 28. These differences between tabs 28 and extension tabs 16, when taken together, allow the passing of set screw 24 distally between extension tabs 16 without having to turn set screw 24 while requiring set screw 24 to be turned when progressing set screw 24 along threaded portions 32 of tabs 28.

Extending along the entire length of the exterior surface of each of extension tabs 16 is a column of horizontally arranged grooves 38. Grooves 38 are divided from one another by a plurality of ridges. Together with grooves 38, the ridges are configured to interact with collar 22 in a ratcheting manner to allow collar 22 to readily slide distally along and between extension tabs 16 while preventing movement thereof proximally. In the preferred embodiment, the ridges between grooves 38 resemble pointed teeth having a distally angled proximal or upper side and a distal or lower side that is essentially perpendicular to a longitudinal axis of screw 12. However, any groove and/or ridge configuration that is capable of allowing linear movement of collar 22 or other suitable ratchet device distally along extension tabs 16 while preventing movement in the opposite direction will suffice.

Referring to FIGS. 3 through 5, collar 22 is composed of a rigid, cylindrical body having a central opening 40 therethrough. Opening 40 has a diameter that is essentially the same as the outer diameter of opposing extension tabs 16 as defined by the ridges on the outer surfaces thereof. Opening 40 is configured for receiving and sliding along opposing extension tabs 16. To prevent the sliding of collar 22 proximally along extension tabs 16, a pair of rigid, elongate, biased pawls 42 are provided on opposing sides of collar 22. Each of pawls 42 has a pivot point 44 coupled to collar 22, an exterior end 48 which is biased against and protrudes outwardly from an exterior surface 50 of collar 22 by a spring 46, and an interior end 52 that protrudes radially inwardly through an inner surface 54 of collar 22 into opening 40. Interior ends 52 are configured for selectively mating with grooves 38 of extension tabs 16 when collar 22 is coupled to the extension tabs. In particular, when collar 22 is coupled to extension tabs 16 and downward pressure is applied to collar 22, interior ends 52 are caused to pivot and ride along the ridges and grooves 38 of extension tabs 16 thereby allowing distal movement of collar 22 along extension tabs 16. However, when upward pressure is placed upon collar 22, interior ends 52 are caught on the ridges and within grooves 38 and no pivoting of pawls 42 occurs by virtue of the geometries of the ridges, grooves 38 and interior ends 52. Consequently, proximal movement of collar is arrested. In the event proximal movement is desired, springs 46 and exterior ends 48 of pawls 42 can be depressed thereby disengaging interiors ends 52 from grooves 38.

Extending from a lower edge of collar 22 are a pair of opposing, rounded protuberances 56 that are arranged below and between opposing pawls 42. Protuberances 56 serve both to properly align collar 22 with extension tabs 16 so that pawls 42 directly engage grooves 38 and to engage and press rod 20 distally into rod seat 30. In particular, when placed onto extension tabs 16, collar 22 is oriented so that protuberances 56 extend between the opposing extension rather along the exteriors surfaces of the tabs.

Figure 7:
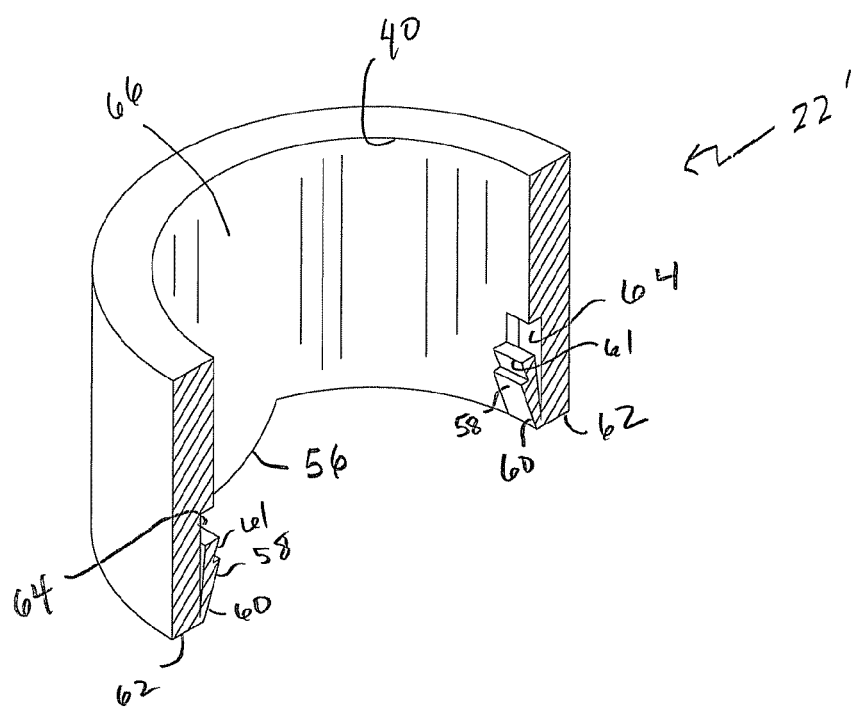
FIG. 7A is a sectional view of an alternative ratchet collar.

Referring to FIGS. 7 and 8, there are depicted two alternatives to collar 22. In particular, FIG. 7 illustrates a cylindrical collar 22' having rigid body and a pair of flexible, elongate opposing pawls 58 each having a lower end 60 integrally formed and extending upwardly from a lower edge 62 of collar 22' and an upper end 61 arranged to protrude radially inwardly through an inner surface 66 of collar 22' and engage grooves 38 of extension tabs 16. Upper end 61 includes a pair of teeth, each tooth having a proximal side that extends substantially perpendicular to a longitudinal axis of screw 12 and a distal or lower side that extends proximally and radially inwardly. Pawls 58 are configured to bend about lower ends 60 to allow the teeth of upper ends 61 to pivot radially outwardly and ride along the ridges and groves 38 of extension tabs 16 when collar 22' is slid distally while preventing proximal movement. Each of pawls 58 is received within a slot 64 formed within inner surface 66 of collar 22' for receiving pawls 64 when pawls 64 are pressed radially outwardly by their interaction with the ridges and grooves 38 of extension tabs 16.

Figure 8A:
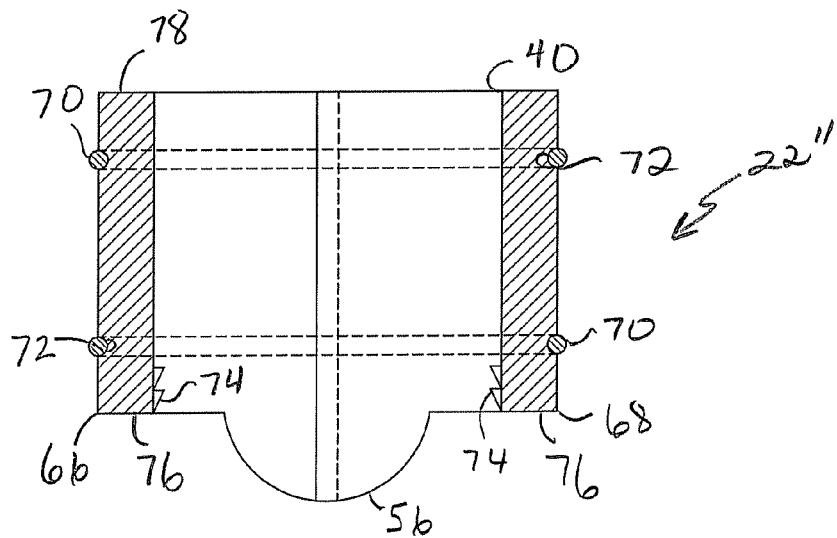
FIG. 8A is sectional view of yet another ratchet collar according to a preferred embodiment of the present invention.
Figure 8B:
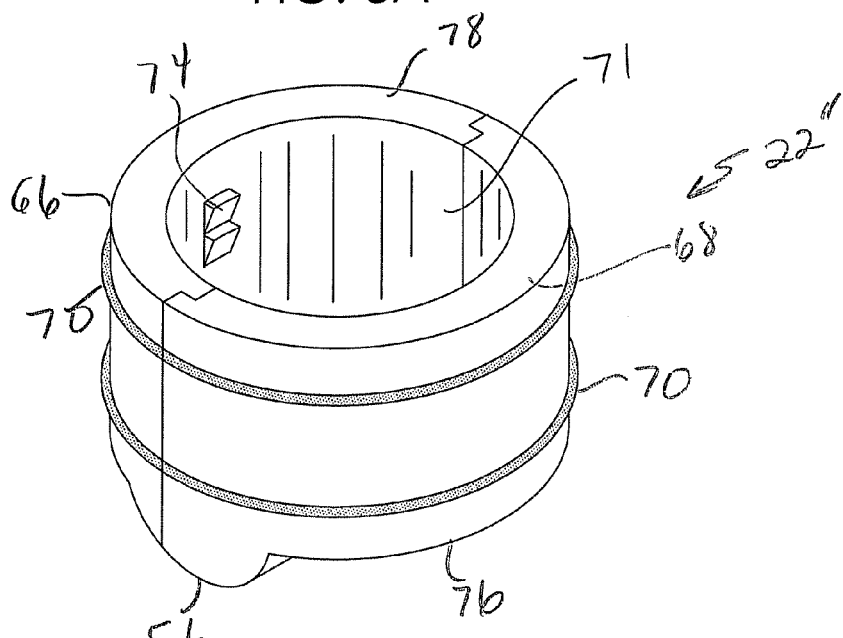
FIG. 8B is a perspective view of the collar of FIG. 8A.

FIGS. 8A and 8B illustrate a cylindrical collar 22'' having rigid body composed of a left half 66 and a right half 68 that are pressed together by a pair of elastic rings 70 circumscribing collar 22''. A pair of grooves 72 encircling and formed within an exterior surface of left 66 and right halves 68 is provided for receiving rings 70 and maintaining rings 70 in place about collar 22''. Extending inwardly from an inner surface 71 of collar 22'' are a plurality of fixed pawls 74 that consist of a pair of teeth like those described for collar 22'. However, unlike pawls 58 of collar 22', pawls 74 are not flexible and are arranged to remain stationary relative to the respective left 66 and right 68 halves from which they extend when engaged with grooves 38. Thus, pawls 74 are biased inwardly by the action of rings 70 which are stretched upon engagement of collar 22'' with extension tabs 16, and more particularly upon the riding of pawls 74 over the ridges formed by grooves 38. Rings 70 bias pawls 74 against grooves 38 thereby enabling pawls 74 and grooves 38 to provide the desired ratcheting effect described above for collars 22 and 22'. As shown in FIG. 8A, pawls 74 can be placed about a lower edge 76 of collar 22'' or adjacent to an upper edge 78 of collar 22'' as depicted in FIG. 8B.

Figure 9:
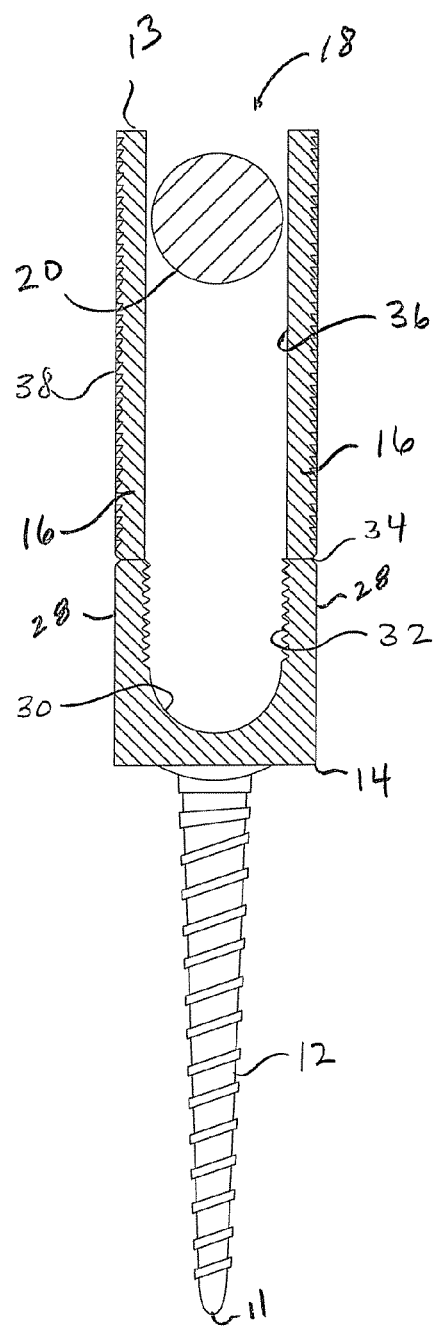
FIG. 9 is a sectional view of the screw and rod fixation assembly of FIG. 1 illustrating placement of the rod into a slot defined by the pair of extension tabs.

FIGS. 9 through 13 illustrate a method for reduction of rod 20 into a plurality of screw heads 14 using collar 22 and set screws 24. Referring to FIG. 9, following anchoring of a number of screws 12 to respective vertebrae, rod 20 is positioned about a proximal end 13 of each of the corresponding assemblies 10 and lowered toward a distal end 11 within rod receiving slot 18 of each such assembly 10. Because of abnormalities in the alignment of the vertebrae, rod 20, which as used herein means a substantially cylindrical body having a desired length, is prevented from readily sliding completely distally within slot 18 of each assembly 10 and seating in rod seats 30.

To aid in the reduction of rod 20 into rod seat 30 of each assembly, collars 22 are placed over the proximal ends 13 and around extension tabs 16 of each of assemblies 10. Each collar 22 is arranged so that respective pawls 42 directly contact extension tabs 16 and grooves 38 and such that protuberances 56 are aligned with the opposing lateral openings of the rod receiving slot 18 of their respective assemblies 10. Each collar 22 is allowed to readily slide distally along tabs 16 by virtue of the ratcheting effect created between pawls 42 and grooves 38. In particular, pawls 42 are allowed to pivot away from extension tabs 16 as teeth 80 of pawls 42 slide over and around the ridges formed by grooves 38 by virtue of the geometries of teeth 80, grooves 38 and the ridges. In this manner, each collar 22 is moved distally along extension tabs 16 until protuberances 56 meet resistance from rod 20.

Figure 10:
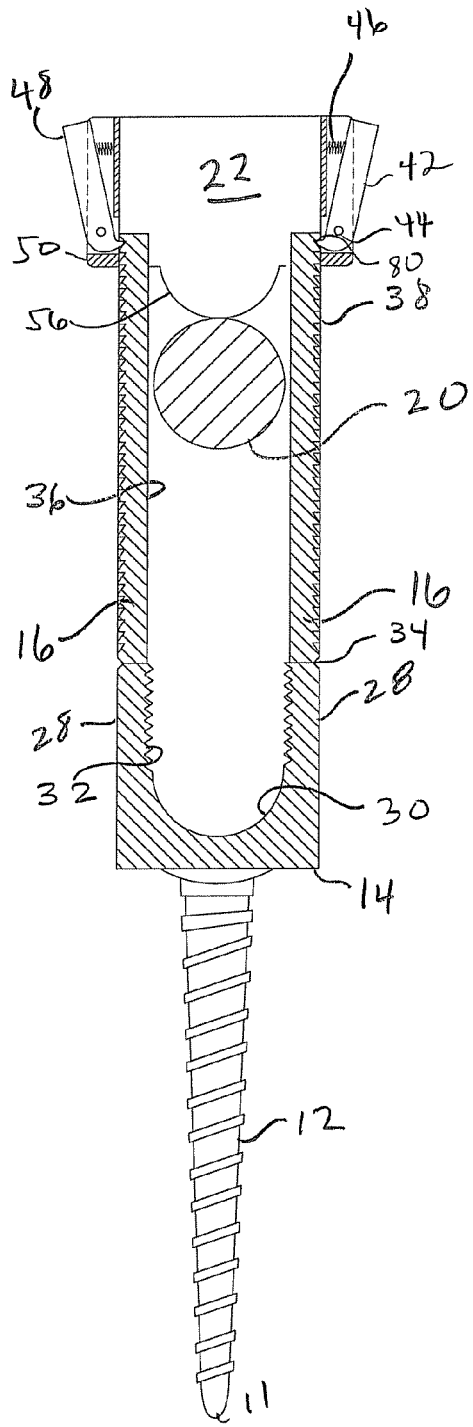
FIG. 10 is a sectional view of the screw and rod fixation assembly of FIG. 1 illustrating coupling of the ratchet collar to the pair of extension tabs.
Figures 11, 12:
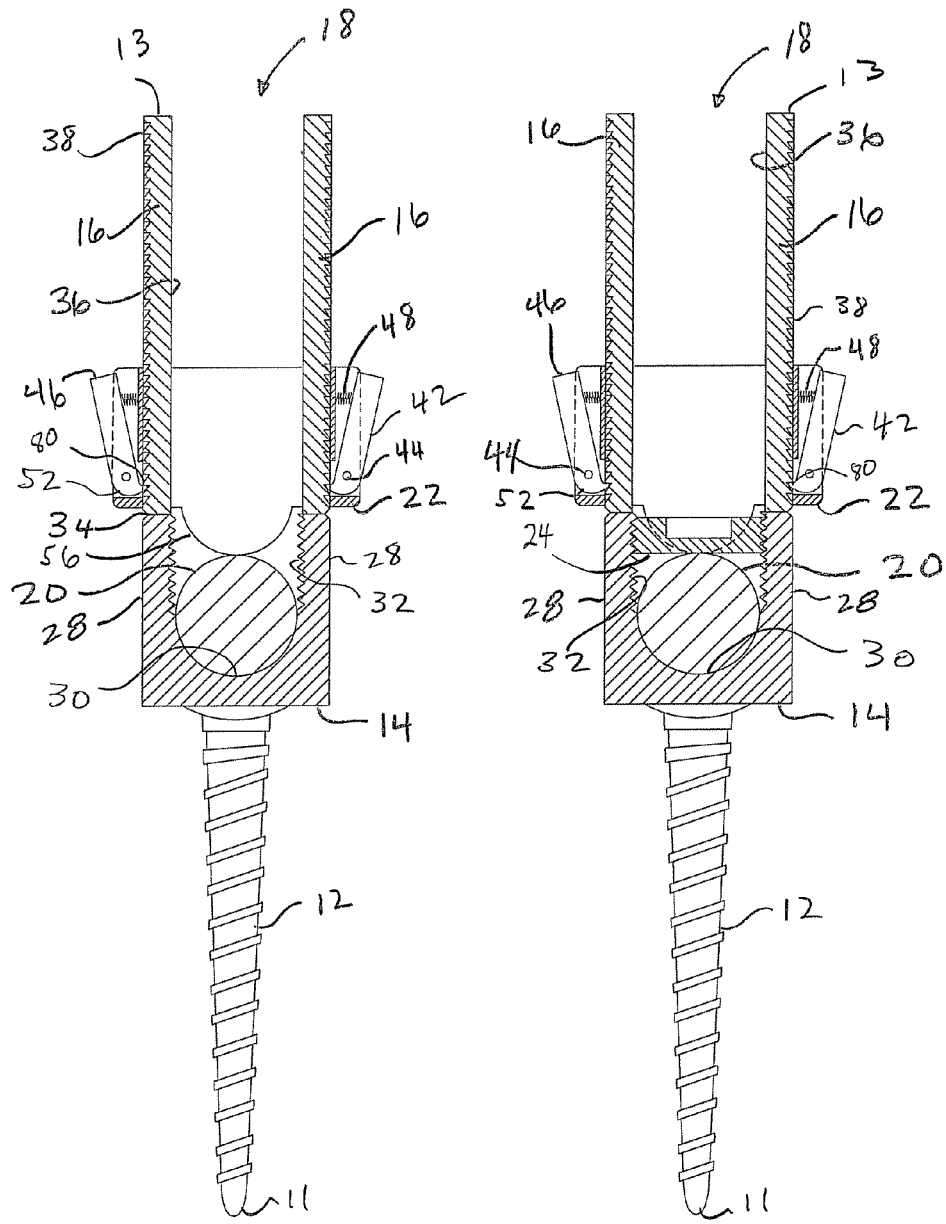
FIG. 11 is a sectional view of the screw and rod fixation assembly of FIG. 1 illustrating use of the ratchet collar to press the rod into a rod seat of the screw.
FIG. 12 is a sectional view of the screw and rod fixation assembly of FIG. 1 illustrating placement of a set screw in between the pair of extension tabs.
Figure 13:
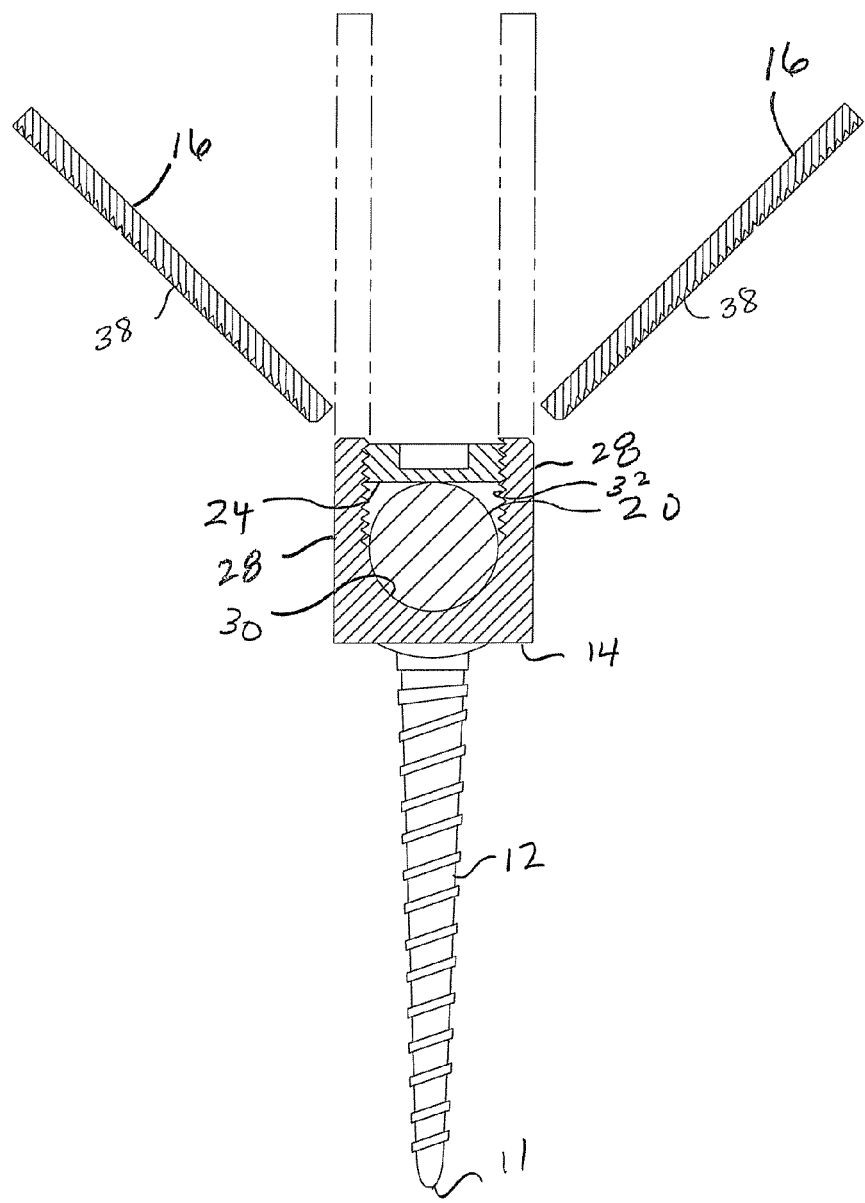
FIG. 13 is a sectional view of the screw and rod fixation assembly of FIG. 1 illustrating removal of the pair of extension tabs and fixing of the rod into a rod seat of the screw.

Referring to FIG. 10, after the resistance posed by 20 is experienced, each of collars 22 must be manually pressed distally to overcome the proximally directed pressure of rod 20. This is accomplished by progressively pressing each of collars 22 in succession toward distal end 11 until the proximally directed pressure exerted by rod 20 is perceived to be great enough to warrant the pressing of other of collars 22, i.e., when the distally directed pressure is great enough to pull screw 12 from the bone. When the manually applied distally directed pressure is discontinued for a particular collar 22, the collar is prevented from sliding proximally by the resulting proximally directed pressured exerted by rod 20 via the interaction of pawls 42 with grooves 38, and more particularly, teeth 80 with the ridges formed between adjacent grooves 38. Teeth 80 are angled to lock within grooves 38 and prevent pivoting of pawls 42 about pivot point 44. This way, as illustrated in FIG. 11, the physician can move from assembly 10 to assembly 10 along a patient's spine and successively reduce rod 20 within each rod seat 30 of assemblies 10. In the event there is a need to slide rod 20 proximally, pawls 42 can be disengaged from grooves 38 by applying pressure to exterior end 48 of each pawl 42 thereby pivoting interior end 52 away from extension tabs 16. This temporarily terminates the ratcheting interaction between collar 22 and tabs 16.

As depicted in FIG. 12, once rod 20 is fully seated within a rod seat, set screw 24 can be inserted between extension tabs 16, through rod receiving slot 18 and opening 40 of collar 22 and screwed into threads 32 of screw head 14 thereby locking rod 20 with screw head 14. Since the rod receiving slot 18 a diameter that is greater than a diameter of set screw 22, set screw 32 can be translated distally through slot 18 without the need of screwing it onto threads. Thus, set screw 32 does not have to be rotated until it enters screw head 14 to engage threads 32 therein. After rod 20 is locked in rod seat 30, extension tabs 16 can be removed from screw head 14 at notches 34 by simply pressing tabs laterally.

As will be apparent to one skilled in the art, various modifications can be made within the scope of the aforesaid description. Such modifications being within the ability of one skilled in the art form a part of the present invention and are embraced by the claims below.

It is claimed:

1. A method for reduction of a rod comprising,
   providing an assembly including,
      a pair of opposing tabs having a proximal end and a distal end, the pair of opposing tabs being coupled to one another about the distal end thereof by a screw head member,
      a decoupling mechanism for decoupling the pair of opposing tabs from the screw head member,
      a rod receiving slot between the pair of opposing tabs, and
      a sliding member configured for coupling to and between the pair of opposing tabs, wherein the sliding member and the pair of opposing tabs are configured for allowing movement of the sliding member distally along the pair of opposing tabs and preventing movement of the sliding member proximally along the pair of opposing tabs,
   inserting the rod into the rod receiving slot,
   coupling the sliding member to the pair of opposing tabs, and
   pushing the sliding member along the pair of opposing tabs toward the distal end thereof thereby directing the rod into a rod seat of the screw head member, wherein the sliding member is pushed along the pair of opposing tabs by a human hand exerting a force directed towards the screw head member.

2. The method according to claim 1 wherein the screw head member is coupled with a pedicle screw.

3. The method according to claim 1 further comprising extending a pawl to and between a tab of the pair of opposing tabs and the sliding member.

4. The method according to claim 3 wherein the pawl is integral with the sliding member and slidably coupled with the tab of the pair of opposing tabs.

5. The method according claim 4 wherein the sliding member includes a release for selectively disengaging the pawl from a pawl receiving groove in the tab of the pair of opposing tabs.

6. The method according to claim 1 wherein the sliding member includes a collar having an opening for receiving the pair of opposing tabs and a set screw therethrough.

7. The method according to claim 6 further comprising receiving the pair of opposing tabs within the opening and extending at least one pawl between the collar and a tab of the pair of opposing tabs.

8. The method according to claim 6 wherein the collar includes at least one protuberance extending from a lower edge thereof, the at least one protuberance being aligned with the rod receiving slot.

9. The method according to claim 1 further comprising pushing the sliding member along the pair of opposing tabs with essentially no rotation of the hand or sliding member about the pair of opposing tabs.

10. The method according to claim 1 further comprising threading a set screw between the pair of opposing tabs and proximal to the rod, the set screw pressing the rod against a rod seat within the screw head member.

11. The method according to claim 1 wherein the sliding member includes a flexible portion.

12. The method according to claim 1 further comprising pushing the sliding member along the pair of opposing tabs with a hand tool.

13. A method for reduction of a rod comprising,
    providing an assembly including,
       extension tabs detachably coupled to a screw head,
       a rod receiving slot formed between the extension tabs,
       a collar, and
       a ratchet mechanism configured for preventing movement in a predetermined direction between the collar and the extension tabs,
    inserting the rod into the rod receiving slot,
    inserting the extension tabs through an opening in the collar,
    pushing the collar along the extension tabs toward the screw head with a hand exerting a force directed towards the screw head, and
    using the ratchet mechanism to prevent movement of the collar away from the screw head.

14. The method according to claim 13 wherein the ratchet mechanism includes at least one pawl.

15. The method according to claim 14 further comprising biasing the at least one pawl toward a central axis of the collar.

16. The method according to claim 13 further comprising coupling the ratchet mechanism to and between the collar and the extension tabs.

17. The method according to claim 13 wherein the ratchet mechanism includes a first portion that is integral with the collar and a second portion that is integral with the extension tabs.

18. The method according to claim 17 further comprising detachably coupling the first portion with the second portion.

19. The method according to claim 17 wherein the first portion includes pawls and the second portion includes pawl receiving grooves.

20. The method according to claim 17 wherein the first portion is movable relative to the collar and the second portion is stationary relative to the extension tabs.

21. The method according to claim 13 wherein the extension tabs have an inner surface devoid of screw threads.

22. The method according to claim 13 further comprising pushing the collar along the extension tabs toward the screw head with essentially no rotation of the hand or the collar.

23. A method for reduction of a rod into a screw having detachable extension tabs comprising,
inserting the rod within a slot formed between the extension tabs,
coupling a sliding member to the extension tabs,
pressing the sliding member against the rod, and
sliding the sliding member and rod together toward the screw with a hand exerting a first force directed towards the screw,
wherein, when the rod exerts a second force against the sliding member, the sliding member is prevented from sliding along the extension tabs away from the screw by a ratchet mechanism.

24. The method according to claim 23 further comprising extending at least one ratchet element of the ratchet mechanism to and between the sliding member and the extension tabs.

25. The method according to claim 24 further comprising receiving the at least one ratchet element within a groove of a plurality of grooves of the ratchet mechanism.

26. The method according to claim 25 further comprising manually disengaging the at least one ratchet element from the groove of the plurality of grooves and sliding the sliding member along the extension tabs away from the screw.

27. The method according to claim 25 further comprising sliding the sliding member and rod together toward the screw with essentially no rotation of the sliding member or the hand.

28. The method according to claim 23 wherein the ratchet mechanism includes a first portion that is integral with the sliding member and a second portion that is integral with the extension tabs.

29. The method according to claim 28 further comprising pivoting the first portion relative to the collar.

30. The method according to claim 23 further comprising using a hand tool to push the sliding member along the extension tabs.

31. The method according to claim 23 wherein the first force is equal to the second force.

* * * * *